(12) United States Patent
Yamamoto (10) Patent No.: US 8,459,324 B2
(45) Date of Patent: Jun. 11, 2013

(54) INTERMITTENT CUTTING TRANSFERRING DEVICE

(75) Inventor: Hiroki Yamamoto, Kanonji (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 13/569,668

(22) Filed: Aug. 8, 2012

(65) Prior Publication Data
US 2012/0297946 A1    Nov. 29, 2012

Related U.S. Application Data (62) Division of application No. 13/286,748, filed on Nov. 1, 2011, now Pat. No. 8,261,801, which is a division of application No. 12/390,106, filed on Feb. 20, 2009, now Pat. No. 8,069,894.

(30) Foreign Application Priority Data

Jun. 30, 2008    (JP) .................................. 2008-171895

(51) Int. Cl.
    *B26D 7/18*    (2006.01)
    *B26D 7/32*    (2006.01)
    *B32B 38/04*    (2006.01)

(52) U.S. Cl.
    USPC ............. 156/519; 271/196; 271/276; 83/100; 83/349

(58) Field of Classification Search
    USPC ..... 156/458, 519, 520; 271/196, 276; 83/100, 83/349
    See application file for complete search history.

(56) References Cited

U.S. PATENT DOCUMENTS

| | | | |
|---|---|---|---|
| 4,671,483 A | 6/1987 | Harbeke | |
| 5,137,758 A | 8/1992 | Kistner et al. | |
| 5,183,252 A | 2/1993 | Wolber et al. | |
| 6,048,120 A | 4/2000 | Kerr | |
| 2004/0250706 A1 | 12/2004 | De Matteis | |
| 2007/0084580 A1 | 4/2007 | Kahl et al. | |

FOREIGN PATENT DOCUMENTS

| | | |
|---|---|---|
| DE | 10012743 | 9/2001 |
| JP | 4-22449 | 2/1992 |
| JP | 8133536 | 5/1996 |

(Continued)

OTHER PUBLICATIONS

Chinese Office Action for Application No. 200980125021.3 mailed Dec. 4, 2012.

(Continued)

*Primary Examiner* — Katarzyna Wyrozebski Lee
*Assistant Examiner* — Scott W Dodds
(74) *Attorney, Agent, or Firm* — Lowe Hauptman Ham & Berner, LLP (57) ABSTRACT

An intermittent cutting transferring device configured to cut a first web into individual sheets and to intermittently transfer the individual sheets onto a second web being continuously fed includes an upper blade roll with a blade and a lower blade roll with an anvil element. Each of the individual sheets cut from the first web is arranged to be guided and transferred onto the second web while the first web is being sucked onto an outer peripheral surface of the lower blade roll by the suction through suction holes formed in a first region on an outer peripheral surface of the lower blade roll. The first region defined as a suction region includes a plurality of the suction holes and a non-suction region does not include the suction holes. The suction region and the non-suction region are provided alternately in a roll rotating direction.

1 Claim, 10 Drawing Sheets

FOREIGN PATENT DOCUMENTS

| | | |
|---|---|---|
| JP | 10218471 | 8/1998 |
| JP | 2005306549 | 11/2005 |
| JP | 2007260875 | 10/2007 |

OTHER PUBLICATIONS

Colombian Office Action for Application No. 11-6447-4 mailed Dec. 20, 2012.

International Search Report for PCT/JP2009/061921 mailed Aug. 18, 2009.

Japanese Office Action for Application No. 2008-171895 mailed Oct. 2, 2012.

Egyptian Office Action for Application No. 2010122205.

Australian Office Action for Application No. 590443 mailed Jan. 24, 2012.

INTERMITTENT CUTTING TRANSFERRING DEVICE

The present application is a divisional of 13/286,748, now U.S. Pat. No. 8,261,801, filed Nov. 1, 2011, which is a divisional of U.S. application Ser. No. 12/390,106, now U.S. Pat. No. 8,069,894, filed Feb. 20, 2009 and is based on, and claims priority from, Japanese Application Number 2008-171895, filed Jun. 30, 2008, the disclosure of which is hereby incorporated by reference herein in its entirety.

BACKGROUND OF THE INVENTION

1. Field of the Invention

The present invention relates to an intermittent cutting transferring device configured to intermittently transfer film sheets to a web being continuously fed after cutting a continuum of film sheet into the film sheets.

2. Description of the Prior Art

An intermittent cutting device is used in processes of manufacturing disposable diaper. Conventionally, the intermittent cutting device is configured to cut a continuum of film sheet printed with patterns such as characters and figures, into film sheets, and to intermittently transfer the film sheets to a web being continuously fed.

Generally, the film sheet is configured to have lower breathability, thinner thickness and more flexibility than the web. That is, the film sheets have characteristics of low rigidity and resilience.

Such an intermittent cutting transferring device includes: an upper blade roll including a blade on an outer peripheral surface; and a lower blade roll including a stationary blade on an outer surface and a mesh suction plate over the entire outer peripheral surface (for example, see Japanese Patent Application Publication No. Hei 10-218471 (pp 4 to 6 and FIG. 3)).

The upper blade roll and the lower blade roll are configured to rotate at approximately the same peripheral speed in directions opposite from each other. In addition, these rolls are also configured to rotate at peripheral velocities higher than the velocity in which the continuum of film sheet is fed to the lower blade roll, and to rotate at a peripheral velocities approximately equal to or lower than the feeding velocity of the web.

Hereinafter, steps of intermittently transferring the film sheet to the web will be described using the intermittent cutting transferring device described above.

In a first step, the intermittent cutting transferring device guides the continuum of film sheet between the blade and the stationary blade while the continuum of film sheet is being sucked onto the outer peripheral surface of the lower blade roll by the suction through the mesh suction plate formed over the entire outer peripheral surface of the lower blade roll.

At this time, the continuum of film sheet slides on the outer peripheral surface of the lower blade roll to be guided between the blade and the stationary blade since the upper blade roll and the lower blade roll rotate at the peripheral velocities higher than the velocity in which the continuum of film sheet is fed to the lower blade roll.

In a second step, the intermittent cutting transferring device intermittently cuts the continuum of film sheet by bringing the blade and the stationary blade into contact with each other, and thus forms a film sheet.

In a third step, the intermittent cutting transferring device guides the cut film sheet to the web while the cut film sheet is being sucked onto the outer peripheral surface of the lower blade roll by the suction through the mesh suction plate formed on the entire outer peripheral surface of the lower blade roll.

In a fourth step, the intermittent cutting transferring device transfers, to the web, the film sheet sucked onto the outer side surface of the lower blade roll.

However, the conventional intermittent cutting transferring device has the following problem. Specifically, the conventional intermittent cutting transferring device is not capable of smoothing out a wrinkle in the continuum of film sheet once the wrinkle is formed, since the suction is performed through the mesh supporting plate formed over the entire outer peripheral surface of the lower blade roll. Particularly, the film sheet has characteristics of low rigidity and resilience, and accordingly cannot be restored to its original state once a wrinkle is formed therein.

Then, the continuum of film sheet is cut by the contact of the blade and the stationary blade with the wrinkle being formed. The cut film sheet is then transferred to the web with the wrinkle being formed.

SUMMARY OF THE INVENTION

The present invention has been made in view of such a situation, and has an object of providing an intermittent cutting transferring device which can suppress the formation of a wrinkle in a continuum of film sheet, and which can smooth out a wrinkle formed in the continuum of film sheet even when the wrinkle is formed therein.

To solve the above situation, the present invention includes the following aspects. A first aspect of the present invention is an intermittent cutting transferring device configured to cut a continuum of film sheet into the film sheets, and to intermittently transfer one of the film sheets which are cut, herein after referred to as "a cut film sheet", to a web being continuously fed. The intermittent cutting transferring device comprises an upper blade roll including a blade on an outer peripheral surface and a lower blade roll including, on an outer peripheral surface, a stationary blade and a plurality of suction holes. The upper blade roll and the lower blade roll rotate at approximately the same peripheral velocity in directions opposite from each other, rotate at the peripheral velocities higher than a velocity in which the continuum of film sheet is fed to the lower blade roll, and rotate at the peripheral velocity equal to or lower than a feeding velocity of the web. The continuum of film sheet is guided between the blade and the stationary blade while the continuum of film sheet is being sucked onto the outer peripheral surface of the lower blade roll by a suction through the suction holes formed in a first region on the outer peripheral surface of the lower blade roll. The continuum of film sheet is intermittently cut by bringing the blade and the stationary blade into contact with each other, and forms the film sheets. The cut film sheet is guided and transferred to the web while the cut film sheet is being sucked onto the outer peripheral surface of the lower blade roll by a suction through the suction holes formed in a second region on the outer peripheral surface of the lower blade roll. The first region is configured of a suction region in which a plurality of the suction holes are formed and a non-suction region in which suction hole is not formed. And the suction region and the non-suction region are provided alternately in a roll peripheral direction.

According to the present invention, the intermittent cutting transferring device can be provided which can suppress the formation of a wrinkle in the continuum of film sheet, and which can smooth out a wrinkle formed in the continuum of film sheet even when the wrinkle is formed therein.

DETAILED DESCRIPTION OF THE PREFERRED EMBODIMENTS

Hereinafter, one example of an intermittent cutting transferring device according to the present invention will be described with reference to the drawings. Note that, throughout the drawings, the same or similar portions are denoted by the same or similar reference numerals. However, the drawings are schematic, and it should be noted that the dimensional proportions and others are different from their actual values.

Thus, specific dimensions and the like should be determined based on the descriptions given below. It is needless to say that the dimensional relationships and dimensional proportions may differ from one drawing to another in some parts.

(Configuration of Intermittent Cutting Transferring Device)

Figure 1:
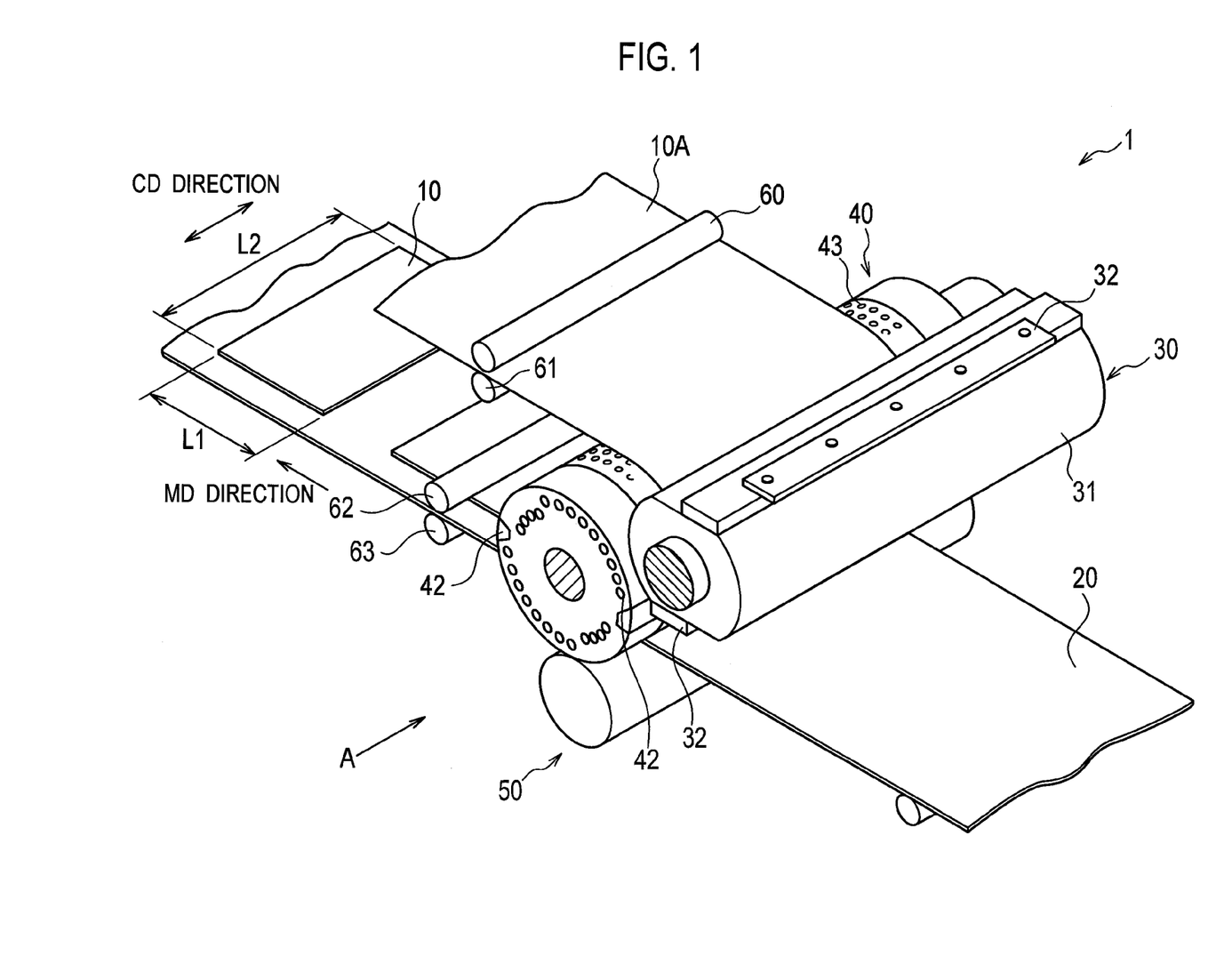
FIG. 1 is a perspective view showing an intermittent cutting transferring device 1 according to this embodiment.
Figure 2:
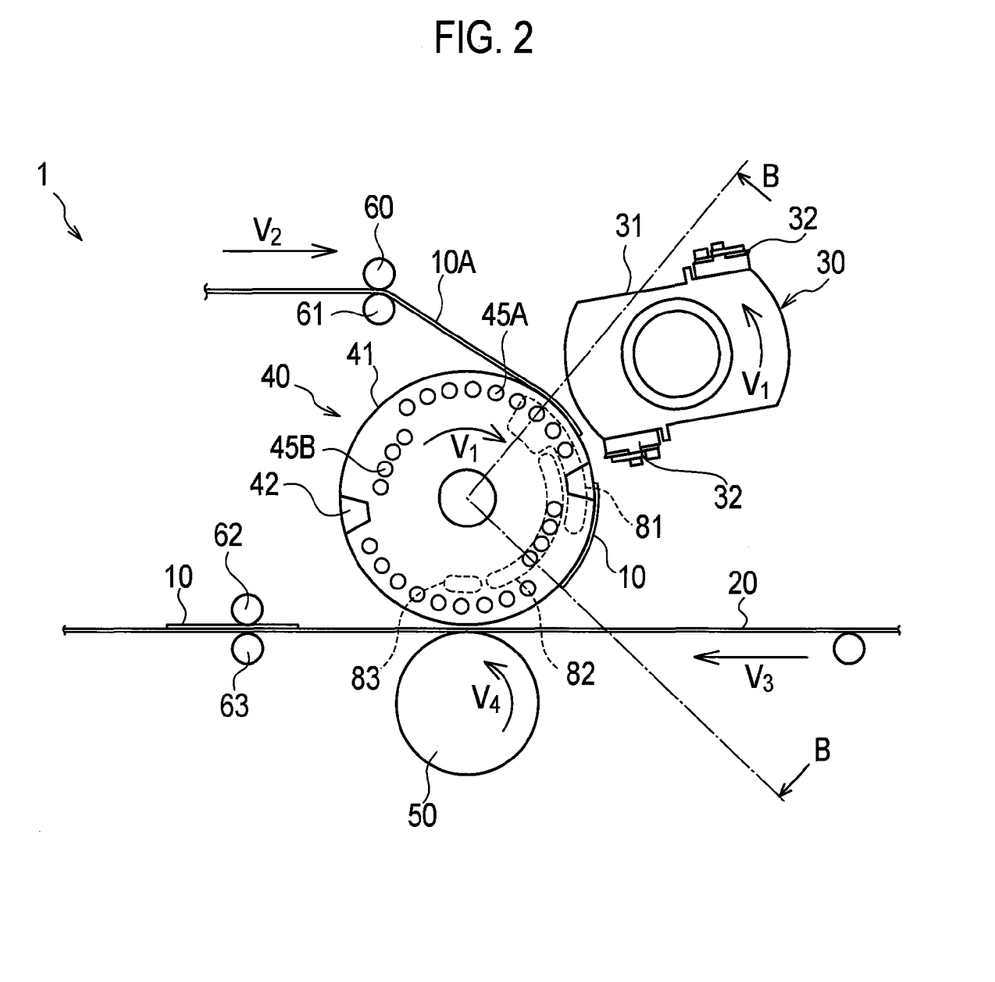
FIG. 2 is a side view (view on arrow A of FIG. 1) showing the intermittent cutting transferring device 1 according to this embodiment.

First, the configuration of the intermittent cutting transferring device according to a first embodiment will be described with reference to the drawings. FIG. 1 is a perspective view showing an intermittent cutting transferring device 1 according to the first embodiment. FIG. 2 is a side view (view on arrow A of FIG. 1) showing the intermittent cutting transferring device 1 according to the first embodiment.

As shown in FIGS. 1 and 2, the intermittent cutting transferring device 1 is configured to intermittently transfer a film sheet 10, obtained by cutting a continuum of film sheet 10A printed with a design such as a character or figure, to a web 20 being fed continuously.

Note that a length (L1) of the cut film sheet 10 in its feeding direction (hereinafter called the "MD direction") is shorter than a length (L2) thereof in a direction orthogonal to the MD direction (this direction is hereinafter called the "CD direction").

The intermittent cutting transferring device 1 is configured briefly of an upper blade roll 30, a lower blade roll 40, and a transfer roll 50.

Two blades 32 are provided on an outer peripheral surface 31 of the upper blade roll 30. The upper blade roll 30 rotates at a peripheral velocity ($V_1$) approximately the same as a peripheral velocity of the lower blade roll 40. The upper blade roll 30 rotates at the peripheral velocity ($V_1$) higher than a velocity ($V_2$) in which the continuum of film sheet 10A is fed to the lower blade roll 40 by a pair of driving rolls 60 and 61. The upper blade roll 30 rotates at the peripheral velocity ($V_1$) approximately the same as a feeding velocity ($V_3$) of the web 20 continuously fed by driving rolls 62 and 63, or rotates at the peripheral velocity ($V_1$) slower than the feeding velocity ($V_3$) of the web 20.

In an outer peripheral surface 41 of the lower blade roll 40, two stationary blades 42 are provided, and suction holes 43 which suck the continuum of film sheet 10A and the cut film sheet 10 are formed. The lower blade roll 40 rotates at the peripheral velocity ($V_1$) approximately the same as the peripheral velocity of the upper blade roll 30, in a direction opposite to the direction in which the upper blade roll 30 rotates. The configuration of the lower blade roll 40 will be described later (see FIG. 3).

The transfer roll 50 brings the web 20 which is continuously fed by the driving rolls 62 and 63 into contact with the lower blade roll 40. The transfer roll 50 rotates at a peripheral velocity ($V_4$) approximately the same as the feeding velocity ($V_3$) of the web 20. In other words, the transfer roll 50 rotates at the peripheral velocity ($V_4$) approximately the same as the peripheral velocity ($V_1$) of the upper blade roll 30 and the lower blade roll 40 described above, or rotates at the peripheral velocity ($V_4$) higher than the peripheral velocity ($V_1$) of the upper blade roll 30 and the lower blade roll 40.

(Configuration of Lower Blade Roll)

Figure 3:
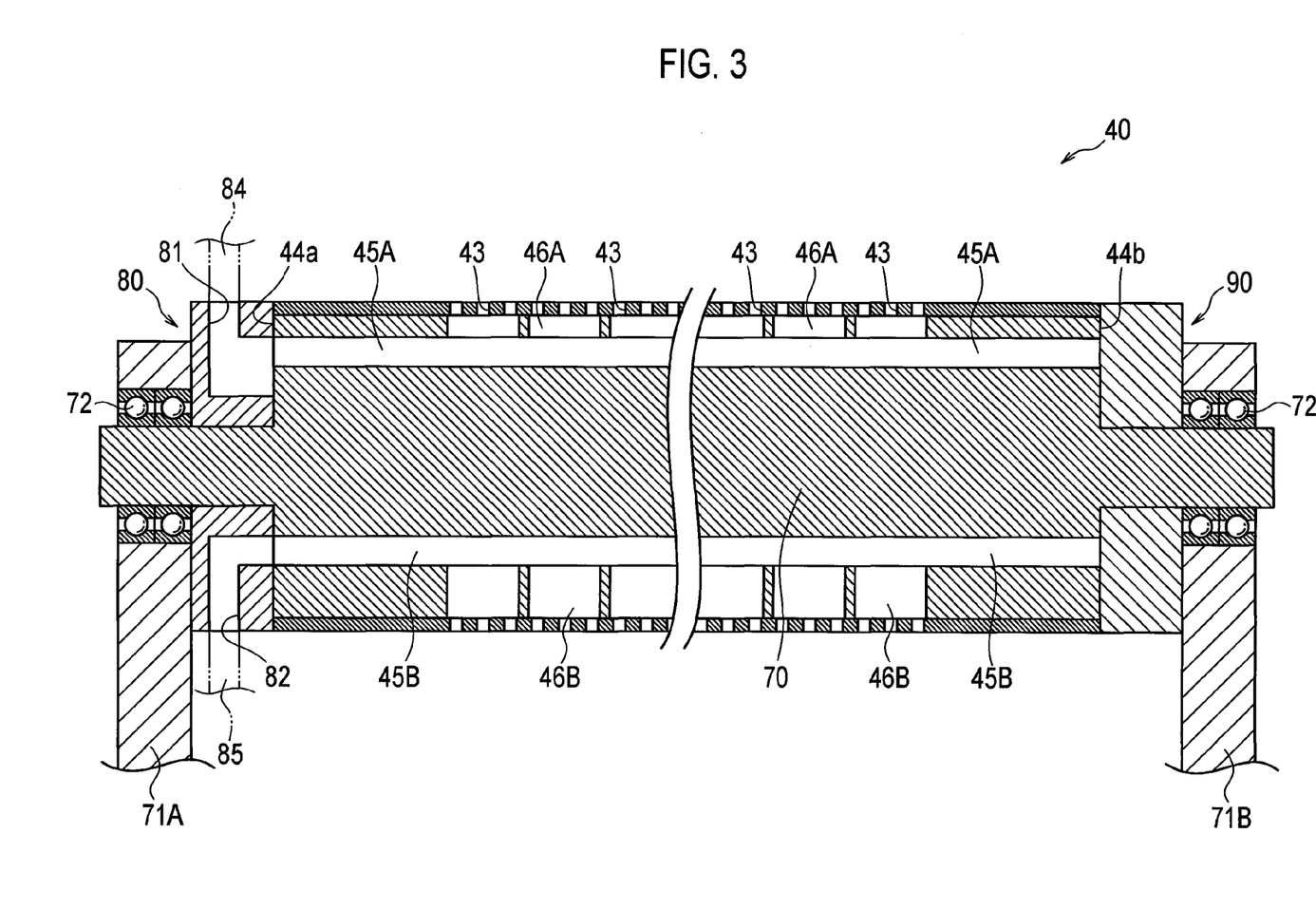
FIG. 3 is a roll width direction sectional view (sectional view along B-B of FIG. 2) showing a lower blade roll 40 according to this embodiment.

Next, the configuration of the lower blade roll 40 described above will be described with reference to the drawings. FIG. 3 is a roll width direction sectional view (sectional view along B-B of FIG. 2) showing the lower blade roll 40 according to the first embodiment.

As shown in FIG. 3, the lower blade roll 40 is formed integrally with a roll shaft 70. The lower blade roll 40 is configured to be rotated between a pair of frames 71A and 71B by shaft bearings 72.

Formed in the lower blade roll 40 are horizontal holes 45A and 45B penetrating from one end surface 44a to the other end surface 44b of the lower blade roll 40 and opening holes 46A and 46B connecting the horizontal holes 45A and 45B and suction holes 43. The suction holes 43 are formed at positions corresponding to the opening holes 46A and 46B.

A suction member 80 is provided between the lower blade roll 40 and the one frame 71A, whereas a sealing member 90 is provided between the lower blade roll 40 and the other frame 71B.

The suction member 80 and the sealing member 90 each have a diameter approximately the same as the diameter of the lower blade roll 40, and are formed in a disk shape. The suction member 80 and the sealing member 90 are fixed to the frames 71A and 71B, respectively, and are configured so as not to rotate together with the lower blade roll 40.

Formed in the suction member 80 are a first suction groove 81 which sucks the continuum of film sheet 10A, a second suction groove 82 which sucks the cut film sheet 10 to guide the cut film sheet 10 to the web 20, and a transfer groove 83 for transferring, on the web 20, the cut film sheet 10 sucked onto the outer peripheral surface 41 of the lower blade roll 40.

The first suction groove 81 is formed at a position corresponding to the horizontal hole 45A formed in the lower blade roll 40, and also to a portion of the outer peripheral surface 41 of the lower blade roll 40 around which the continuum of film sheet 10A is wound. The first suction groove 81 is connected with a suction connection pipe 84 connecting the first suction groove 81 and suction air supply means (not shown) which sucks air in the horizontal hole 45A.

The second suction groove 82 is formed at a position corresponding to the horizontal hole 45B formed in the lower blade roll 40, and to a portion of the outer peripheral surface 41 of the lower blade roll 40 around which the cut film sheet 10 is wound. The second suction groove 82 is connected with a suction connection pipe 85 connecting the second suction groove 82 and suction air supply means (not shown) which sucks air in the horizontal hole 45B.

The transfer groove 83 is formed at a position corresponding to the horizontal hole 45B formed in the lower blade roll 40, and to a portion to which the cut film sheet 10 is transferred. The transfer groove 83 is connected with a transfer connection pipe (not shown) connecting the transfer groove 83 and air releasing means (not shown) which releases the suction of air performed by the suction air supply means.

Note that the air releasing means does not necessarily need to release the suction of air performed by the suction air supply means, and may be configured to blow out air through the transfer groove 83 (transfer connection pipe).

In this embodiment, the suction member 80 is provided between the lower blade roll 40 and the one frame 71A. However, it is not limited to this configuration, and the suction member 80 may be additionally provided, instead of the sealing member 90, between the lower blade roll 40 and the other frame 71B. That is, the suction air supply means may perform supply of air from both end sections of the horizontal holes 45A and 45B.

(Alignment of Suction Holes)

Figure 4:
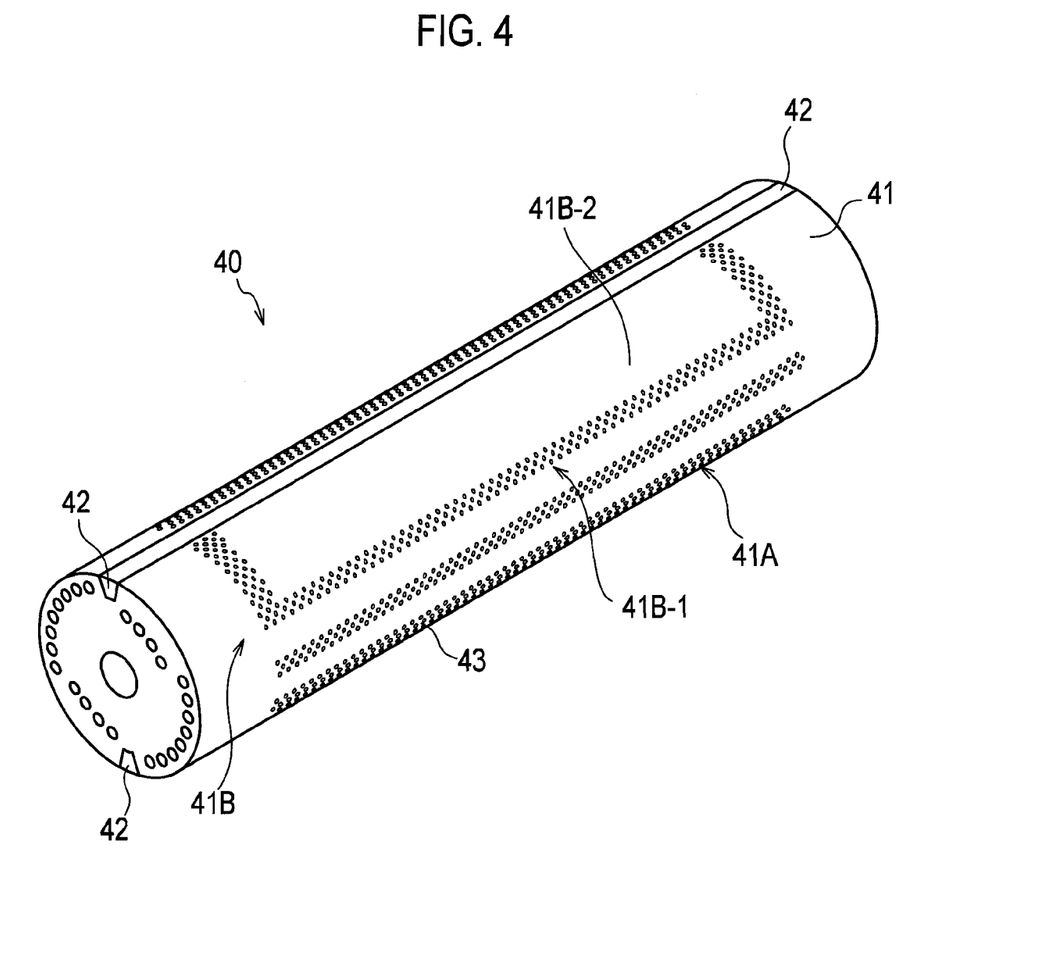
FIG. 4 is a perspective view showing the lower blade roll 40 according to this embodiment.
Figure 5:
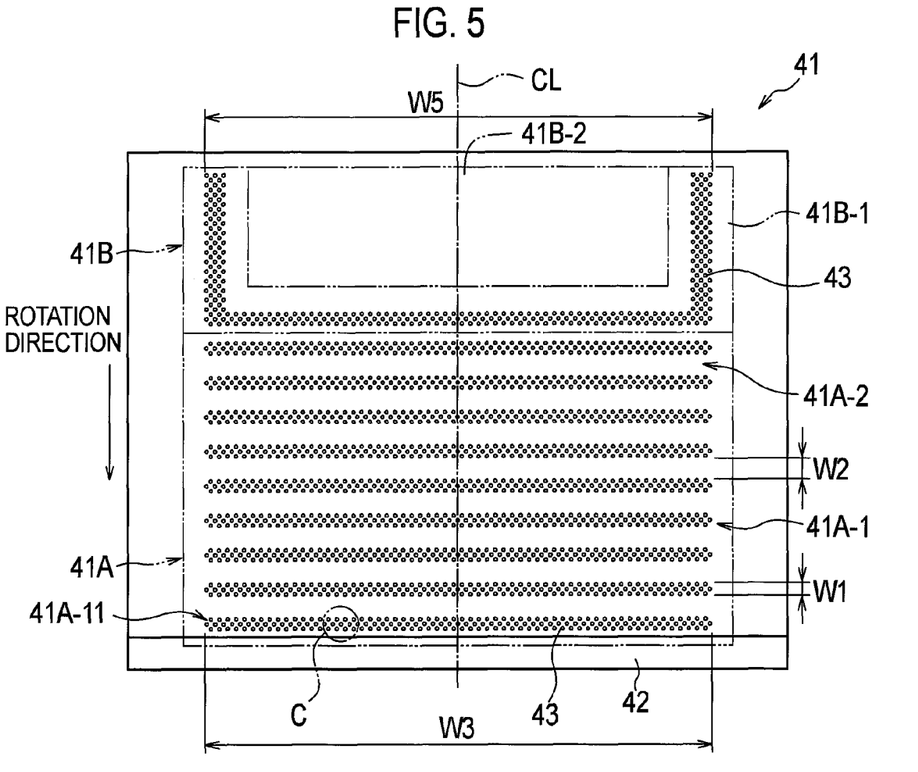
FIG. 5 is a development view showing the lower blade roll 40 according to this embodiment.
Figure 6:
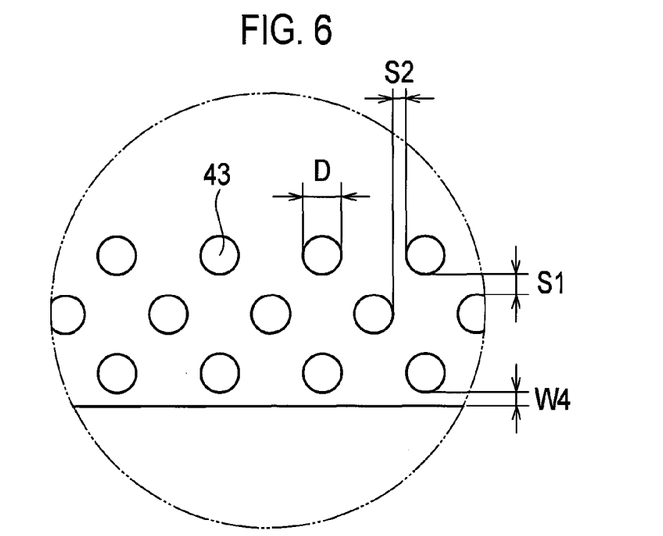
FIG. 6 is an enlarged view showing the vicinity of suction holes according to this embodiment.
Figure 7:
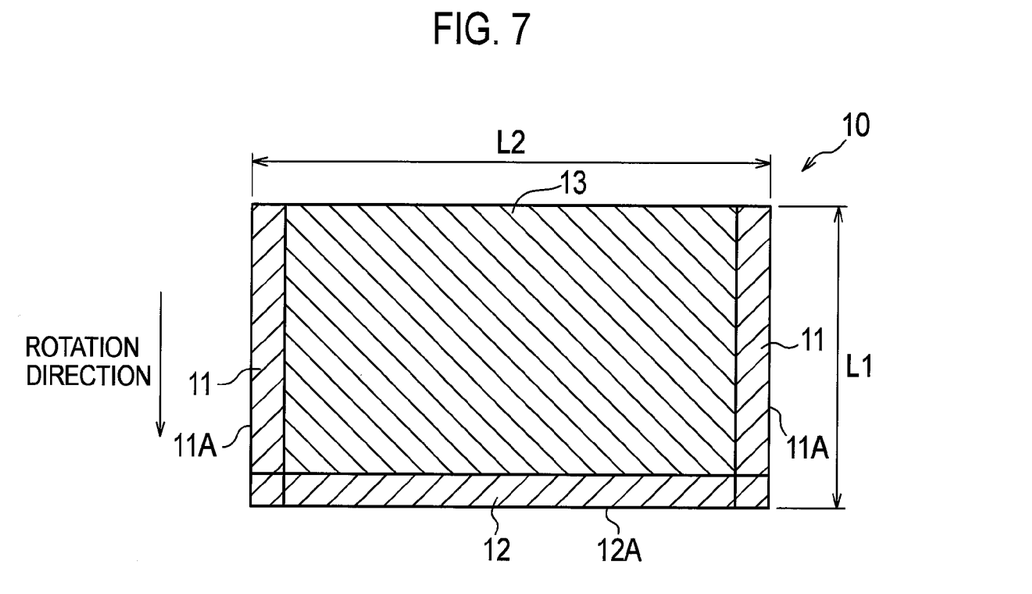
FIG. 7 is an upper view showing a film sheet according to this embodiment.

Next, the alignment of the suction holes 43 provided in the lower blade roll 40 described above will be described with reference to the drawings. FIG. 4 is a perspective view showing the lower blade roll 40 according to this embodiment. FIG. 5 is a development view showing the lower blade roll 40 according to this embodiment. FIG. 6 is an enlarged view (enlarged view of C in FIG. 5) showing the vicinity of the suction holes according to this embodiment. FIG. 7 is an upper view showing the film sheet according to this embodiment.

As shown in FIGS. 4 and 5, the suction holes 43 are formed in a first region 41A and in a second region 41B on the outer peripheral surface 41 of the lower blade roll 40.

In the first region 41A and in the second region 41B, the suction holes 43 are arranged at predetermined intervals in the roll peripheral direction and in the roll width direction, and are aligned such that the suction holes 43 that are adjacent in the roll peripheral direction are displaced from each other in the roll width direction (a so-called staggered alignment).

Specifically, as shown in FIG. 6, a distance (51) in the roll peripheral direction between one suction hole 43 of the suction holes 43 and another suction hole 43 adjacent to the one suction hole 43 in the roll peripheral direction is configured to be smaller than the diameter (D) of the suction hole 43.

A distance (S2) in the roll width direction between one suction hole 43 of the suction holes 43 and another suction hole 43 adjacent to the one suction hole 43 in the roll peripheral direction is configured to be smaller than the diameter (D) of the suction hole 43. The first region 41A is configured of suction regions 41A-1 each of which having the multiple suction holes 43 formed therein, and non-suction regions 41A-2 each of which having no suction hole 43 formed therein. Accordingly, the suction holding force in the suction regions 41A-1 is stronger than the suction holding force in the non-suction regions 41A-2.

The suction regions 41A-1 and the non-suction regions 41A-2 are provided in the roll width direction. The suction regions 41A-1 and the non-suction regions 41A-2 are provided alternately in the roll peripheral direction.

It is configured so that a width (W1) of each suction region 41A-1 in the roll peripheral direction would be shorter than a width (W2) of each non-suction region 41A-2 in the roll peripheral direction.

It is configured so that a width (W3) of each suction region 41A-1 in the roll width direction would be wider than the length (L2) of the cut film sheet 10 in the CD direction.

Behind the stationary blade 42 in the roll rotation direction, a width (W4) in the roll peripheral direction between a suction region 41A-11 closest to the stationary blade 42 and the stationary blade 42 is configured to be smaller than the width (W2) of the non-suction region 41A-2 in the roll peripheral direction. Particularly, the width (W4) is preferably smaller than the diameter (D) of the suction hole 43, and is more preferably made as small as possible.

The second region 41B is configured of an edge area 41B-1 having the multiple suction holes 43 formed therein, and a center area 41B-2 having no suction hole 43 formed therein. Accordingly, the suction holding force in the edge area 41B-1 is stronger than the suction holding force in the center area 41B-2.

The edge area 41B-1 faces both side edge regions 11 and a front end region 12 formed ahead in the proceeding direction of the film sheet 10.

As shown in FIG. 7, the both side edge regions 11 of the cut film sheet 10 show regions within 25% of the length (L2) in the CD direction with both end sections 11A of the cut film sheet 10 as the references. The front end region 12 of the cut film sheet 10 formed ahead in the proceeding direction shows a region within 50% of the length (L1) in the MD direction with a front end section 12A of the film sheet as the reference. Note that the area of the center area 41B-2 needs to have an area that is 50% or more of a whole area of the cut film sheet 10.

A maximum width (W5) of the edge area 41B-1 in the roll width direction is approximately equivalent to the width (W3) of the suction region 41A-1 in the roll width direction described above, i.e., configured to be wider than the length (L2) of the cut film sheet 10 in the CD direction.

The center area 41B-2 faces a remaining region 13 which is a region other than the both side edge regions 11 and the front end region 12 formed ahead in the proceeding direction of the cut film sheet 10. Note that, as shown in FIG. 7, the remaining region 13 shows a region inside the both side edge regions 11 and the front end region 12 formed ahead in the proceeding direction of the cut film sheet 10 described above.

(Operation of Intermittent Cutting Transferring Device)

Next, the operation of the intermittent cutting transferring device 1 according to the first embodiment will be described briefly.

In a first step, the intermittent cutting transferring device 1 guides the continuum of film sheet 10A to between the blade 32 and the stationary blade 42 with the continuum of film sheet 10A being sucked on the outer peripheral surface 41 of the lower blade roll 40 by the suction of the suction air supply means through the suction holes 43 formed in the first region 41A (suction region 41A-1) on the outer peripheral surface 41 of the lower blade roll 40.

At this time, the continuum of film sheet 10A slides on the outer peripheral surface 41 of the lower blade roll 40 to be guided to between the blade 32 and the stationary blade 42 because the upper blade roll 30 and the lower blade roll 40 rotate at the peripheral velocity ($V_1$) faster than the velocity ($V_2$) at which the continuum of film sheet 10A is supplied to the lower blade roll 40.

In a second step, the intermittent cutting transferring device 1 intermittently cuts the continuum of film sheet 10A by bringing the blade 32 and the stationary blade 42 into contact with each other. The cut film sheet 10 is thus formed. Note that the length (L1) of the cut film sheet 10 in the MD direction is shorter than the length (L2) of the cut film sheet 10 in the CD direction.

In a third step, the intermittent cutting transferring device 1 guides the cut film sheet 10 onto the web 20 with the cut film sheet 10 being sucked on the outer peripheral surface 41 of the lower blade roll 40 by the suction of the suction air supply means through the suction holes 43 formed in the second region 41B (edge area 41B-1) on the outer peripheral surface 41 of the lower blade roll 40.

In a fourth step, the intermittent cutting transferring device 1 transfers the cut film sheet 10 sucked on the outer side surface 41 of the lower blade roll 40 onto the web 20 by causing the air releasing means to release the suction of air performed by the suction air supply means.

(Operation and Effect)

In the intermittent cutting transferring device 1 according to this embodiment, the first region 41A is configured of the suction region 41A-1 and the non-suction region 41A-2, and the suction region 41A-1 and the non-suction region 41A-2 are provided alternately in the roll peripheral direction. Accordingly, the continuum of film sheet 10A comes into a flat state on the non-suction region 41A-2 when the continuum of film sheet 10A slides on the outer peripheral surface 41 of the lower blade roll 40 to be guided to between the blade 32 and the stationary blade 42 (i.e., before being cut).

The continuum of film sheet 10A is held in the flat state on the outer peripheral surface 41 of the lower blade roll 40 while being sucked on the flat state on the outer peripheral surface 41 of the lower blade roll 40. That is, the operation of holding the continuum of film sheet 10A in the suction region 41A-1 on the outer peripheral surface 41 of the lower blade roll 40 in the flat state can be constantly repeated by the rotation of the lower blade roll 40 with the continuum of film sheet 10A being in the flat state in the non-suction region 41A-2. Thus, the formation of a wrinkle in the continuum of film sheet 10A can be suppressed. Even when a wrinkle is formed in the continuum of film sheet 10A, the wrinkle formed in the continuum of film sheet 10A can be smoothed out.

In the intermittent cutting transferring device 1 according to this embodiment, the width (W1) of the suction region 41A-1 in the roll peripheral direction is configured to be shorter than the width (W2) of the non-suction region 41A-2 in the roll peripheral direction. Accordingly, the continuum of film sheet 10A slides a longer distance on the non-suction region 41A-2 when sliding on the outer peripheral surface 41 of the lower blade roll 40, thereby easily coming into the flat state on the non-suction region 41A-2 (i.e., on a flat surface). Thus, the formation of a wrinkle in the continuum of film sheet 10A can be suppressed.

In the intermittent cutting transferring device 1 according to this embodiment, the suction holes 43 are arranged at predetermined intervals in the roll peripheral direction and in the roll width direction, and are aligned such that the suction holes 43 that are adjacent in the roll peripheral direction are displaced from each other in the roll width direction. Accordingly, it becomes easier to uniformly hold the continuum of film sheet 10A slid on the outer peripheral surface 41 of the lower blade roll 40 in the flat state. Thus, the formation of a wrinkle in the continuum of film sheet 10A can be suppressed.

Particularly, the distance (S1) in the roll peripheral direction between one suction hole 43 of the suction holes 43 and another suction hole 43 adjacent to the one suction hole 43 in the roll peripheral direction is configured to be smaller than the diameter (D) of the suction hole 43. The distance (S2) in the roll width direction between one suction hole 43 of the suction holes 43 and another suction hole 43 adjacent to the one suction hole 43 in the roll peripheral direction is configured to be smaller than the diameter (D) of the suction hole 43. Thus, it becomes easier to uniformly hold the continuum of film sheet 10A slid on the outer peripheral surface 41 of the lower blade roll 40 in the flat state.

The continuum of film sheet 10A has a possibility of being crumpled by the contact of the blade 32 and the stationary blade 42. Thus, the width (W4) between the suction region 41A-1 and the stationary blade 42 in the roll peripheral direction is configured to be smaller than the width (W2) of the non-suction region 41A-2 in the roll peripheral direction. Particularly, the width (W4) is preferably smaller than the diameter (D) of the suction hole 43, and more preferably made as small as possible. Accordingly, the continuum of film sheet 10A is sucked on the outer peripheral surface 41 of the lower blade roll 40 by the suction through the suction holes 43 formed in the suction region 41A-11 immediately after being cut by the contact of the blade 32 and the stationary blade 42. Thus, the continuum of film sheet 10A can be prevented from being folded or bent.

Modified Example

It has been described that the suction region 41A-1 according to the embodiment described above is provided in the roll width direction, but it may be modified as follows. Note that the same portions as those in the intermittent cutting transferring device 1 (lower blade roll 40) according to the embodiment described above are denoted by the same reference numerals, and differing portions will mainly be described.

(1) Modified Example 1

Figure 8:
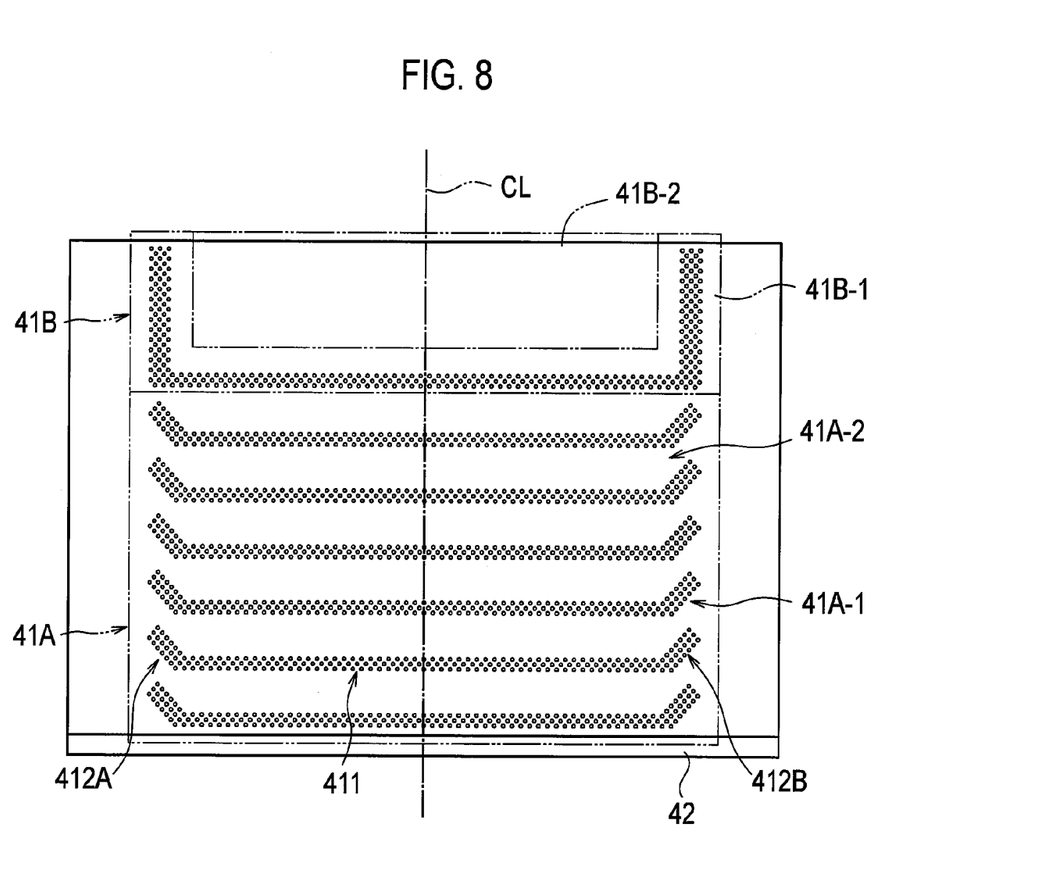
FIG. 8 is a development view showing the lower blade roll 40 according to Modified Example 1.

FIG. 8 is a development view showing the lower blade roll 40 according to Modified Example 1. As shown in FIG. 8, the suction region 41A-1 is provided to be symmetrical with respect to a center line (CL) passing through the center of the roll width direction as the reference. Note that the center line (CL) does not necessarily need to be the center of the roll width direction as long as it is the center of the cut film sheet 10 (continuum of film sheet 10A) in the CD direction, and it is needless to say that it may be the center between the pair of frames 71A and 71B, for example.

Specifically, the suction region 41A-1 is configured of a width direction region 411 in the roll width direction and inclined regions 412A and 412B located in end sections of the width direction region 411 and inclined to the roll width direction.

The inclined regions 412A and 412B are inclined to have a wider distance therebetween to a direction opposite to the roll rotation direction. That is, the one inclined region 412A is inclined in a different direction from the other inclined region 412B.

The suction holes 43 formed in the suction region 41A-1 are aligned in the inclined region 412A and the inclined region 412B. That is, the suction holes 43 in the inclined regions 412A and 412B are aligned to have a wider distance therebetween in a direction opposite to the roll rotation direction.

In the intermittent cutting transferring device 1 according to Modified Example 1, the inclined regions 412A and 412B are inclined to have a wider distance therebetween in a direction opposite to the roll rotation direction. Accordingly, the continuum of film sheet 10A is pulled toward the outside in the roll rotation direction and the roll width direction. Thus, even when a wrinkle is formed in the continuum of film sheet 10A, the wrinkle formed in the continuum of film sheet 10A can be smoothed out.

(2) Modified Example 2

Figure 9:
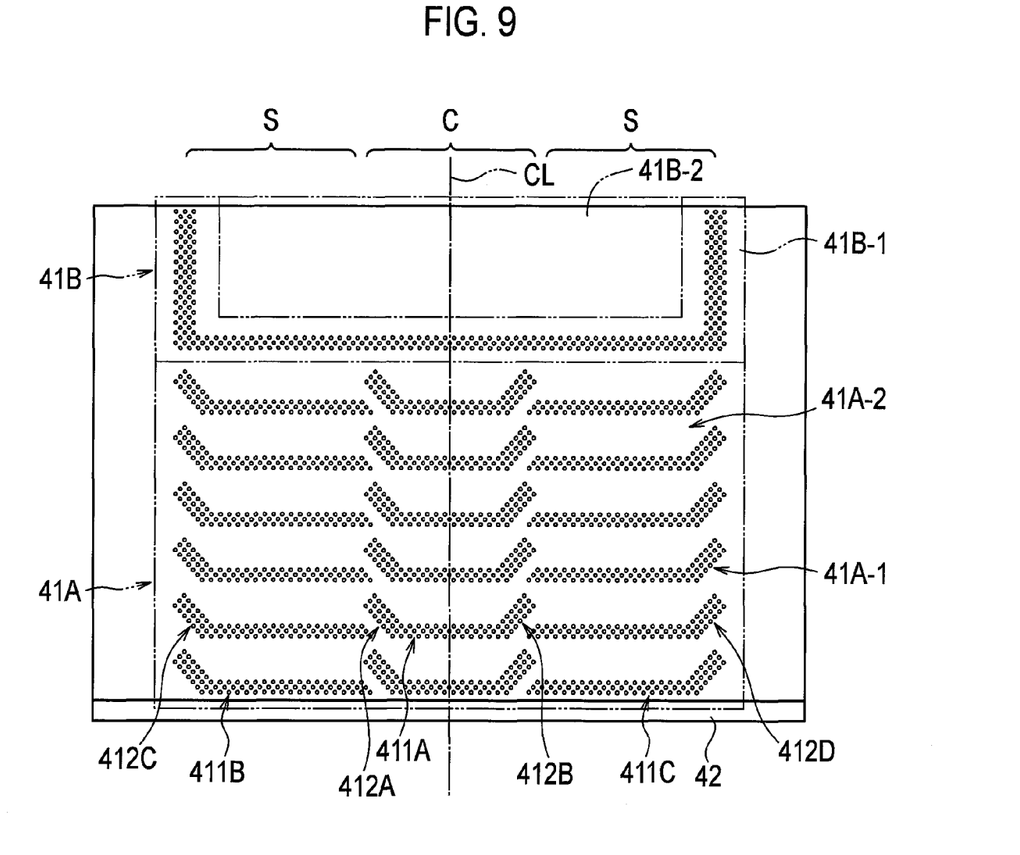
FIG. 9 is a development view showing the lower blade roll 40 according to Modified Example 2.

FIG. 9 is a development view showing the lower blade roll 40 according to Modified Example 2. As shown in FIG. 9, the suction region 41A-1 is provided to be symmetrical with respect to the center line (CL) as the reference.

Specifically, the suction region 41A-1 is configured of a center area C provided on the center line (CL) and an outside region S provided on the outside of the center area C in the roll width direction.

The center area C is configured of a width direction region 411A in the roll width direction and inclined regions 412A and 412B respectively located in end sections of the width direction region 411A and inclined to the roll width direction.

The outside region S is configured of width direction regions 411B and 411C in the roll width direction and inclined regions 412C and 412D located in end sections of the width direction regions 411B and 411C on the outside in the roll width direction and inclined to the roll width direction. Note that the inclined region 412C is provided to be approximately parallel to the inclined region 412A, and the inclined region 412D is provided to be approximately parallel to the inclined region 412B.

The inclined regions 412A to 412D are inclined to have a wider distance therebetween in a direction opposite to the roll rotation direction with the center line (CL) as the reference. That is, the inclined regions 412A and 412C are inclined in a direction different from the inclined regions 412B and 412D.

The suction holes 43 formed in the suction region 41A-1 are aligned in the width direction regions 411A to 411C and the inclined regions 412A to 412D. That is, the suction holes 43 in the inclined regions 412A to 412D are aligned to have a wider distance therebetween in a direction opposite to the roll rotation direction with the center line (CL) as the reference.

In the intermittent cutting transferring device 1 according to Modified Example 2, the inclined regions 412A to 412D are inclined to have a wider distance therebetween in a direction opposite to the roll rotation direction, whereby the same operation and effect as those of the intermittent cutting transferring device 1 of Modified Example 1 can be obtained.

(3) Modified Example 3

Figure 10:
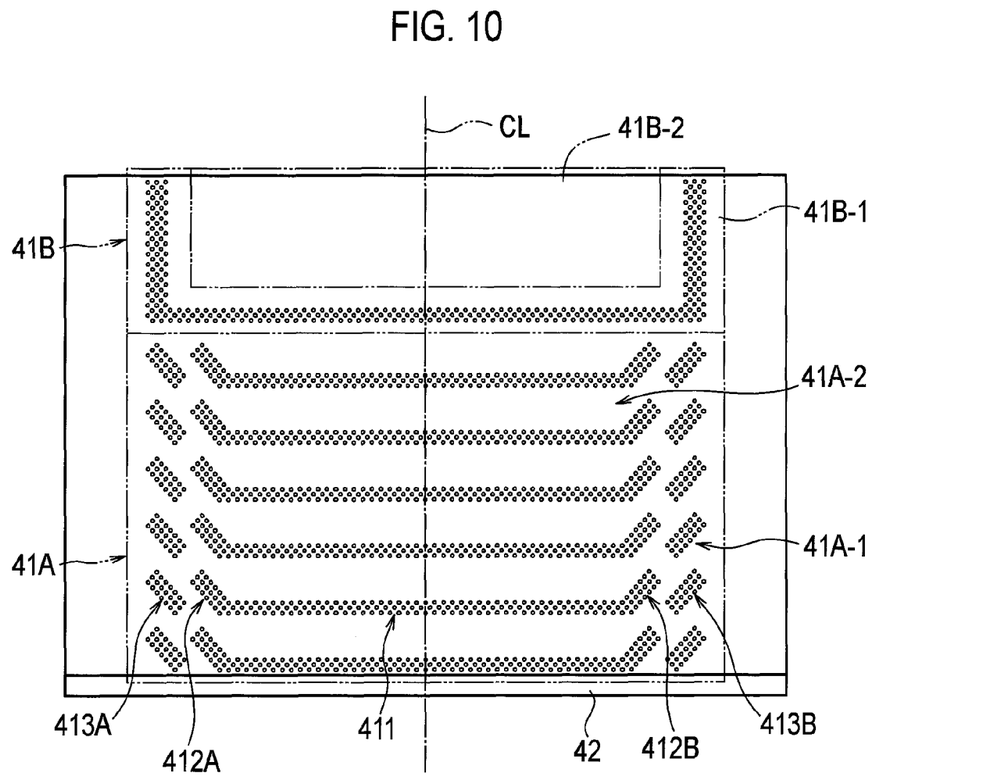
FIG. 10 is a development view showing the lower blade roll 40 according to Modified Example 3.

FIG. 10 is a development view showing the lower blade roll 40 according to Modified Example 3. As shown in FIG. 10, the suction region 41A-1 is provided to be symmetrical with respect to the center line (CL) as the reference.

Specifically, the suction region 41A-1 is configured of: the width direction region 411 in the roll width direction; the inclined regions 412A and 412B located in the end sections of the width direction region 411 and inclined to the roll width direction; and distant regions 413A and 413B distant from the inclined regions 412A and 412B in the roll width direction.

The inclined regions 412A and 412B are inclined to have a wider distance therebetween in a direction opposite to the roll rotation direction. That is, the one inclined region 412A is inclined in a direction different from the other inclined region 412B.

The distant regions 413A and 413B are provided to be approximately parallel to the inclined regions 412A and 412B, respectively. That is, the distant region 413A is provided to be approximately parallel to the inclined region 412A. The distant region 413B is provided to be approximately parallel to the inclined region 412B.

The suction holes 43 formed in the suction region 41A-1 are aligned along the width direction region 411, the inclined regions 412A and 412B, and the distant regions 413A and 413B, respectively. That is, the suction holes 43 along the inclined regions 412A and 412B and the distant regions 413A and 413B are aligned to have a wider distance therebetween in a direction opposite to the roll rotation direction.

In the intermittent cutting transferring device 1 according to Modified Example 3, the inclined regions 412A and 412B and the distant regions 413A and 413B are inclined to have a wider distance therebetween in a direction opposite to the roll rotation direction, whereby the same operation and effect as those of the intermittent cutting transferring device 1 according to Modified Examples 1 and 2 can be obtained.

(4) Modified Example 4

Figure 11:
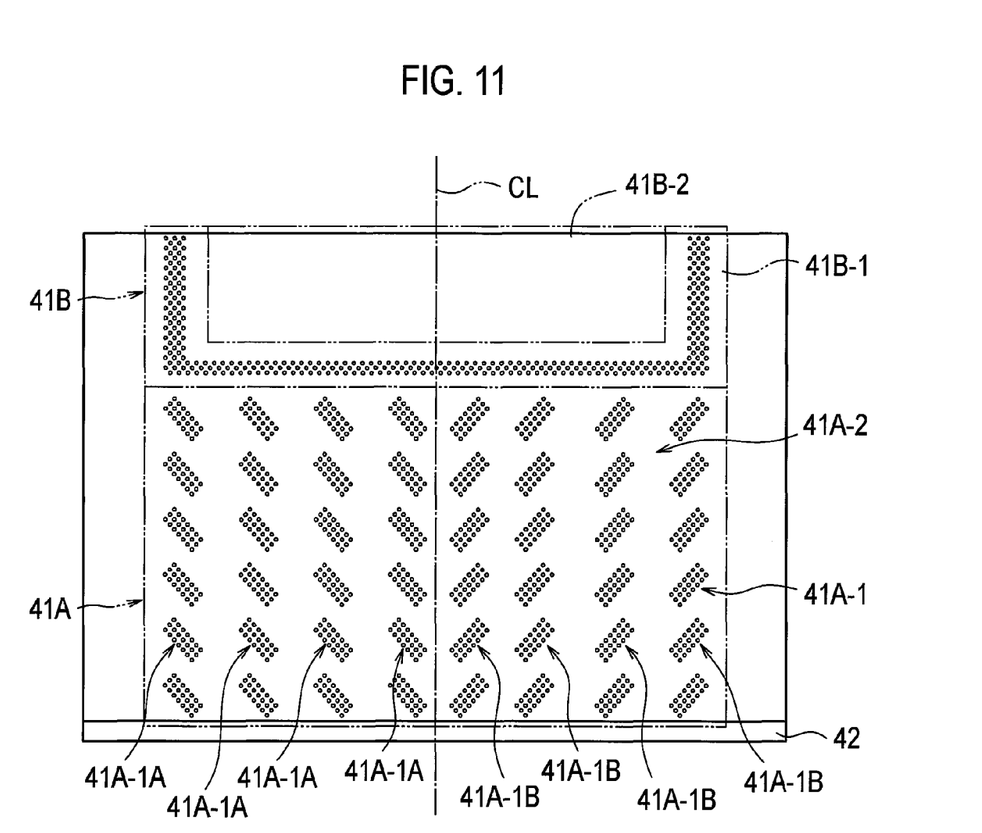
FIG. 11 is a development view showing the lower blade roll 40 according to Modified Example 4.

FIG. 11 is a development view showing the lower blade roll 40 according to Modified Example 4. As shown in FIG. 11, the suction regions 41A-1 are provided to be symmetrical with respect to the center line (CL) as the reference.

Specifically, multiple suction regions 41A-1 are provided in the roll peripheral direction and the roll width direction. That is, the suction regions 41A-1 are provided to be spaced away from each other in the roll peripheral direction and the roll width direction.

The suction regions 41A-1 are inclined with respect to the roll width direction. A suction region 41A-1A located on one side of the center line (CL) as the reference is inclined in a direction different from a suction region 41A-1B located on the other side.

The suction holes 43 formed in the suction region 41A-1 are aligned along the respective separate suction regions 41A-1. That is, the suction holes 43 form inclinations to have a wider distance therebetween in a direction opposite to the roll rotation direction with the center line (CL) as the reference. The suction holes 43 formed along the suction region 41A-1 located on one side with respect to the center line (CL) as the reference are aligned toward directions different from the suction holes 43 formed along the suction region 41A-1B located on the other side.

In the intermittent cutting transferring device 1 according to Modified Example 3, the suction region 41A-1 is inclined with respect to the roll width direction such that the suction region 41A-1A located on one side of the center line (CL) as the reference is inclined in a direction different from the suction region 41A-1B located on the other side. Accordingly, the same operation and effect as those of the intermittent cutting transferring device 1 according to Modified Examples 1 to 3 can be obtained.

Other Embodiments

As described above, the content of the present invention has been disclosed through the embodiments of the present invention. However, the descriptions and the drawings forming a part of the disclosure should not be construed to limit the present invention.

In the embodiments, it has been described that two blades 32 are provided on the outer peripheral surface 31 of the upper blade roll 30, but it is not limited thereto. At least one blade 32 may be provided. In the same manner, at least one stationary blade 42 may be provided on the outer peripheral surface 41 of the lower blade roll 40.

In the embodiments, it has been described that the first region 41A extends in the roll width direction (the width direction region). However, it is not limited to this, and it is needless to say that various combinations of Modified Examples 1 to 4 can be applied.

In the embodiments, it has been described that the second region 41B is configured of the edge area 41B-1 and the center area 41B-2, but it is not limited thereto. It is needless to say that the configuration may be the same as that of the first region 41A.

Various alternative embodiments, examples, and application technology will become apparent to those skilled in the art from this disclosure. Thus, the technical scope of the present invention is defined only by the claims appropriate from the descriptions above.

What is claimed is:

1. An intermittent cutting transferring device configured to cut a first web into individual sheets and to intermittently transfer the individual sheets onto a second web being continuously fed, said device comprising:
   an upper blade roll including a blade on an outer peripheral surface thereof; and
   a lower blade roll including, on an outer peripheral surface thereof, an anvil element and a plurality of suction holes, wherein
   the upper blade roll and the lower blade roll are rotatable in opposite roll rotating directions at approximately the same peripheral velocity which is higher than a velocity in which the first web is fed to the lower blade roll, and equal to or lower than a feeding velocity of the second web,
   the blade and the anvil element are configured to guide the first web therebetween while the first web is being sucked onto the outer peripheral surface of the lower blade roll by a suction through the plurality of suction holes formed in a first region of the outer peripheral surface of the lower blade roll,
   the blade and the anvil element are adapted to be brought into contact with each other to intermittently cut the first web into the individual sheets,
   each of the individual sheets cut from the first web is arranged to be guided and transferred onto the second web while the sheet is being sucked onto the outer peripheral surface of the lower blade roll by a suction through the suction holes formed in a second region on the outer peripheral surface of the lower blade roll,
   the first region includes a suction region in which the plurality of the suction holes are formed and a non-suction region free of said suction holes,
   the suction region and the non-suction region are provided alternately in the roll rotating direction of the lower blade roll, a closest distance between adjacent suction holes in the roll rotating direction of the lower blade roll and a closest distance between adjacent suction holes in a roll width direction substantially perpendicular to the roll rotating direction are smaller than a diameter of each said suction hole, wherein
   the suction region includes a plurality of first and second inclined regions, in each of which the suction holes are arranged in separated rows inclined to the roll width direction, and
   the separated rows of suction holes in the first and the second inclined regions converge toward each other in the roll rotating direction of the lower blade roll.

* * * * *